US009198793B2

(12) United States Patent
Bonutti

(10) Patent No.: US 9,198,793 B2
(45) Date of Patent: Dec. 1, 2015

(54) FINGER ORTHOSIS

(71) Applicant: Bonutti Research, Inc., Effingham, IL (US)

(72) Inventor: Peter M. Bonutti, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 0 days.

(21) Appl. No.: 14/183,942

(22) Filed: Feb. 19, 2014

(65) Prior Publication Data
US 2014/0171847 A1 Jun. 19, 2014

Related U.S. Application Data

(63) Continuation of application No. 13/231,419, filed on Sep. 13, 2011, now Pat. No. 8,679,043, and a continuation of application No. 12/181,520, filed on Jul. 29, 2008, now Pat. No. 8,038,637, and a continuation of application No. 11/181,238, filed on Jul. 14, 2005, now Pat. No. 7,404,804, and a continuation of application No. 10/329,895, filed on Dec. 26, 2002, now Pat. No. 6,921,377, and a continuation of application No. 09/664,922, filed on Sep. 18, 2000, now Pat. No. 6,502,577.

(51) Int. Cl.
*A61F 5/00* (2006.01)
*A61F 5/01* (2006.01)
*A61H 1/02* (2006.01)

(52) U.S. Cl.
CPC .............. *A61F 5/013* (2013.01); *A61H 1/0288* (2013.01); *A61F 2005/0137* (2013.01); *A61F 2005/0153* (2013.01)

(58) Field of Classification Search
CPC .... A61B 5/021; A61B 5/681; A61B 17/0206; A61B 17/025; A61B 17/28; A61B 17/29; A61B 17/3423; A61B 17/3476; A61B 19/26; A61B 2017/2808; A61B 2017/320044; A61B 2017/349; A61B 2019/4889; A61B 17/2909; A61F 2/4455; A61F 2005/0137; A61F 2005/0153; A61F 5/013; A61F 11/08; A61F 11/12; A61F 13/00008; A61F 13/00034; A61F 13/00063; A61F 13/00068; A61F 13/041; A61F 13/10; A61F 13/141; A61F 5/05866; A61F 5/0118; A61F 5/10; A61F 2/7843; A61F 2005/0144; A61F 5/05858; A61F 5/05875; A61F 5/3753; A61H 1/0288
USPC ........................................ 602/20–22; 128/880
See application file for complete search history.

(56) References Cited

U.S. PATENT DOCUMENTS

| | | | | |
|---|---|---|---|---|
| 3,794,019 | A | * | 2/1974 | Ritland et al. ................... 602/22 |
| 5,324,251 | A | * | 6/1994 | Watson .......................... 602/16 |
| 5,328,448 | A | * | 7/1994 | Gray, Sr. ......................... 602/22 |
| 5,681,269 | A | * | 10/1997 | Basaj et al. ..................... 602/22 |
| 8,679,043 | B2 | * | 3/2014 | Bonutti .......................... 602/16 |

* cited by examiner

*Primary Examiner* — Michael Brown
(74) *Attorney, Agent, or Firm* — Senniger Powers LLP

(57) ABSTRACT

A finger orthosis for moving a joint and configured to move a joint is provided. The finger orthosis includes a hand cuff and an actuating mechanism coupled to the hand cuff. The actuating mechanism comprises an actuator member, an externally threaded member and a frame. Methods of using the finger orthosis to move a joint between a first and second portion of a finger are also provided.

12 Claims, 5 Drawing Sheets

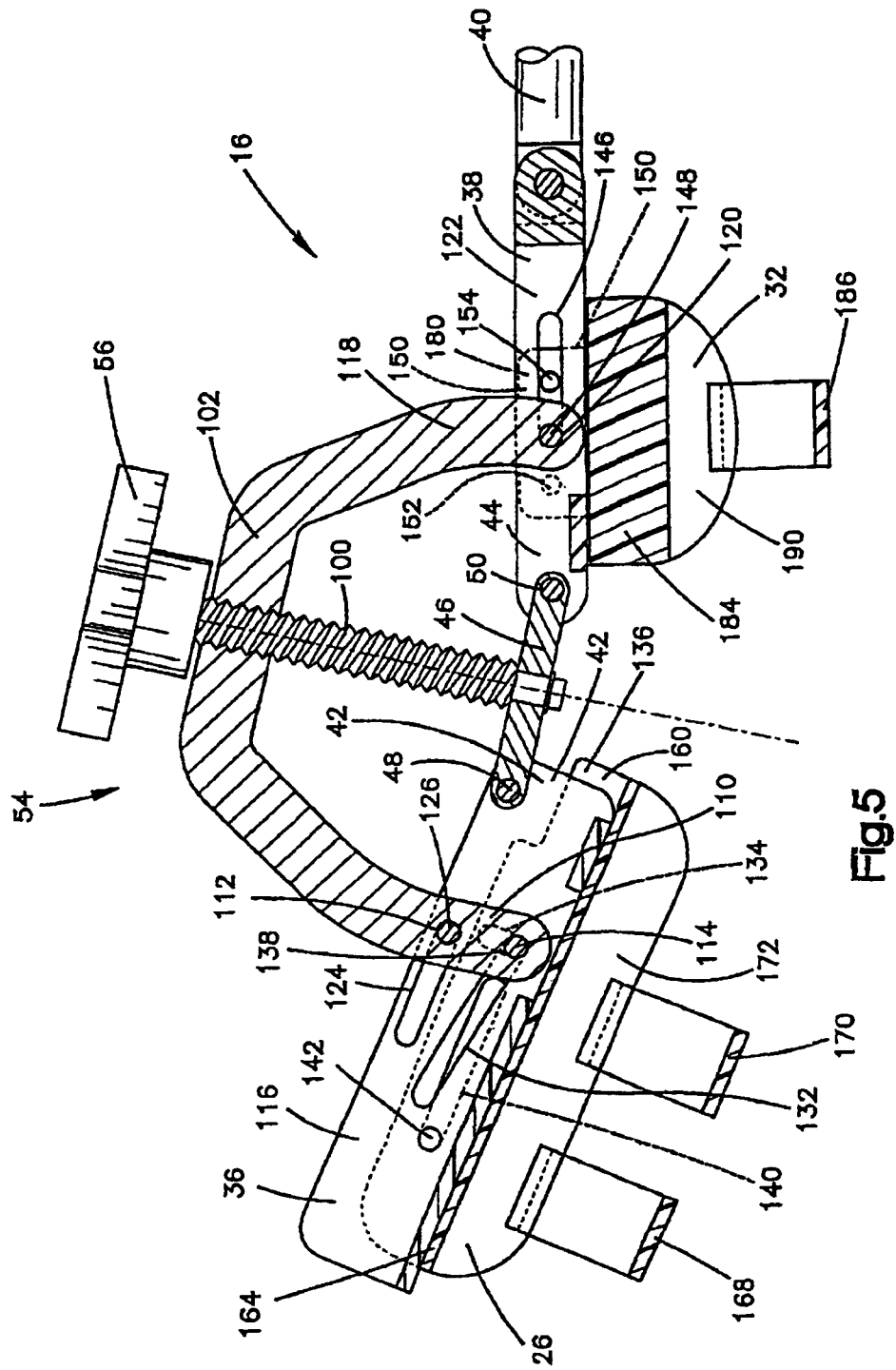

FINGER ORTHOSIS

CROSS REFERENCE TO RELATED APPLICATIONS

This application is a continuation application of U.S. patent application Ser. No. 13/231,419, filed Sep. 13, 2011, which is a continuation of U.S. patent application Ser. No. 12/181,520, filed Jul. 29, 2008 (now U.S. Pat. No. 8,038,637), which is a continuation of U.S. patent application Ser. No. 11/181,238, filed Jul. 14, 2005 (now U.S. Pat. No. 7,404,804), which is a continuation of U.S. patent application Ser. No. 10/329,895, filed Dec. 26, 2002 (now U.S. Pat. No. 6,921,377), which is a continuation of U.S. patent application Ser. No. 09/664,922, now U.S. Pat. No. 6,502,577, the entire content of these applications is expressly incorporated herein by reference thereto.

BACKGROUND OF THE INVENTION

The present invention relates to new and improved method for moving joints of fingers.

A known splint for supporting and injuring hand is disclosed in U.S. Pat. No. 4,765,320. The splint disclosed in this patent allows movement of the fingers of the hand and urges the fingers toward an extended condition under the influence of elastic bands.

A known joint extension splint is disclosed in U.S. Pat. No. 5,681,269. The splint disclosed in this patent has an adjustable finger support for a joint of the finger. Support sections of the support are connected to portions of the finger on opposite sides of the joint. A screw jack operates with hinged attachments to the undersides of the support sections to provide controlled extension of the finger.

SUMMARY OF THE INVENTION

The present disclosure provides a finger orthosis for moving a joint of a finger. The finger orthosis comprises a hand cuff configured to couple to a hand connected to a finger and an actuating mechanism coupled to the hand cuff. The actuating mechanism comprises an actuator member, an externally threaded member and a frame. The present disclosure also provides a finger orthosis configured to move a joint of a finger comprising the hand cuff and actuating mechanism.

The present disclosure also provides a method of using a finger orthosis to move a joint between first and second portions of a finger. The method comprises coupling a hand cuff to a hand, wherein the hand is connected to a finger, and applying force to an actuating mechanism coupled to the hand cuff. The actuating mechanism comprises an actuator member, an externally threaded member and a frame. When the force is applied to the actuating mechanism, the actuator member moves along an axis which extends through the joint.

BRIEF DESCRIPTION OF THE DRAWINGS

The foregoing and other features of the invention will become more apparent upon consideration of the following description taken in connection with the accompanying drawings, wherein:

FIG. 5 is an enlarged sectional view of the portion of the orthosis, generally similar to FIG. 4, depicting the manner in which the orthosis is operated to move the finger in extension.

DESCRIPTION OF THE INVENTION

Orthosis—General Description

Figure 1:
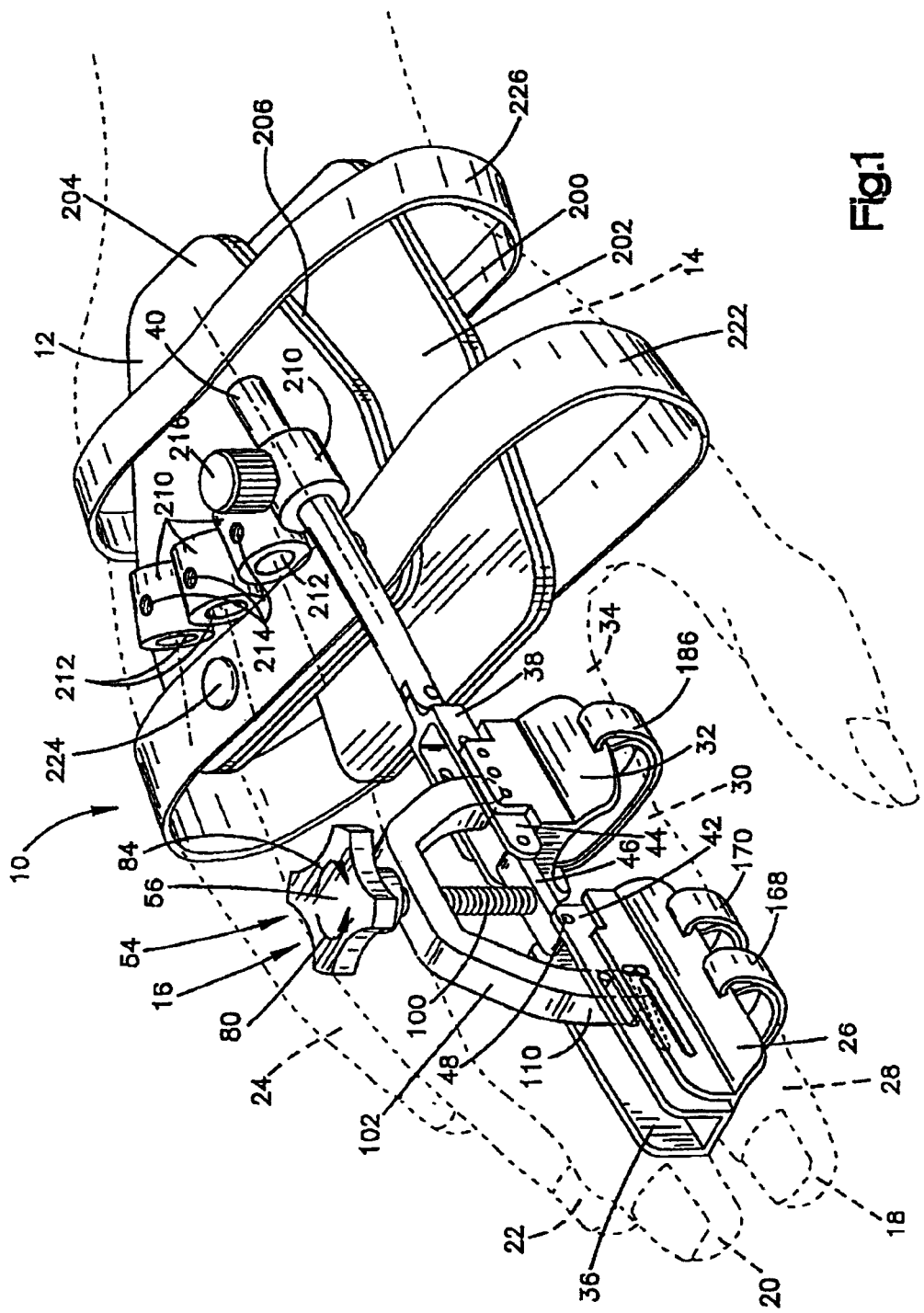
FIG. 1 is an illustration of an orthosis constructed in accordance with the present invention and mounted on a hand with a mechanism which can be operated to move a finger of the hand.

An orthosis 10 (FIG. 1) can be used to sequentially move different fingers of the same hand. The orthosis 10 includes a hand cuff 12 which is connected with a hand 14 of a person. A bending mechanism 16, operable to move a joint of a finger, can be connected to an index finger 18, a middle finger 20, a ring finger 22, or a little finger 24 of the hand 14. The bending mechanism 16 is shown connected to the index finger 18 in FIG. 1. Furthermore, more than one bending mechanism 16 may be connected to more than one of the fingers 18-24.

A first finger cuff 26 of the bending mechanism 16 is connected with a first portion 28 of the index finger 18 connected to a joint 30 of the index finger. A second finger cuff 32 of the bending mechanism 16 is connected to a second portion 34 of the finger 18 connected to the joint 30. The cuffs 12, 26, and 32 may have any desired construction as long as they are effective to engage the hand 14 and the first and second portions 28 and 34 of the finger 18.

A first cuff arm 36 is connected with the first finger cuff 26. A second cuff arm 38 is connected with the second finger cuff 32. A connecting portion 40 of the bending mechanism 16 is connected with the hand cuff 12. The connecting portion 40 is pivotally connected to the second cuff arm 38. The connecting portion 40 connects the bending mechanism 16 to the hand cuff 12 in alignment with the finger 18.

End portions 42 and 44 (FIGS. 1-3) of the cuff arms 36 and 38 are spaced apart and interconnected by a base link or actuator member 46. The first cuff arm 38 is pivotally connected to the actuator member 46 at a pivot connection 48. The pivot connection 48 is offset from the joint 30 on a side of the joint toward a tip of the finger 18. The second cuff arm 38 is pivotally connected to the actuator member 46 at a pivot connection 50. The pivot connection 50 is offset from the joint 30 on a side of the joint away from the tip of the finger 18. The cuff arms 36 and 38 are pivotal about spaced apart parallel axes at the pivot connections 48 and 50.

An actuator mechanism 54 transmits force to simultaneously pivot the cuff arms 36 and 38 about the pivot connections 48 and 50 and to move the finger cuffs 26 and 32 along the cuff arms. The actuator mechanism 54 transmits force from an input member which, in the illustrated embodiment of the orthosis 10, is a manually rotatable knob 56. Force is transmitted from the knob 56 through the actuator mechanism 54 to the actuator member 46. Force is transmitted from the actuator member 46 to pivot the cuff arms 36 and 38 about the pivot connections 48 and 50. In addition, force is transmitted from the knob 56 to move the finger cuffs 26 and 32 along the cuff arms 36 and 38 as the cuff arms are pivoted about the pivot connections 48 and 50.

The actuator mechanism 54 is operable to move the cuff arms 36 and 38 from an initial position, such as the one shown in FIG. 1, to actuated positions, such as those shown in FIGS.

2 and 3. Operation of the actuator mechanism 54 moves the actuator member 46 along a path extending through the joint 30 of the finger 18. As this occurs, the cuff arms 36 and 38 are pivoted about parallel spaced apart axes which extend through the pivot connections 48 and 50 and are perpendicular to the longitudinal central axes of the cuff arms 36 and 38.

As the inner end portions 42 and 44 of the cuff arms 36 and 38 are moved, the finger cuffs 26 and 32 move along the cuff arms. The movement of the finger cuffs 26 and 32 reduces the amount of distraction applied to the finger 18. This enables the finger 18 to be moved without being distracted or compressed. Although it is advantageous to move the finger 18 without either compressing or distracting the soft tissue in the finger, there is a slight controlled distraction of the soft tissue in order to be certain that compression of the finger is avoided.

When the finger cuffs 26 and 32 (FIGS. 2 and 3) are connected with the finger 18, the cuff arms 36 and 38 are disposed at a back side of the finger 18 opposite the palm of the hand 14. Thus, the cuff arms 36 and 38 are disposed in an outer sector having a center at the finger joint 30 and radians which are coincident with longitudinal central axes of the portions 28 and 34 of the finger 18. The longitudinal central axis of the portion 28 of the finger 18 has been indicated at 60 and the longitudinal central axis of the portion 34 of the finger has been indicated at 62. The axes 60 and 62 intersect at a center 64 of the joint 30. The outer sector includes the are indicated by arrows 66 and 68 indicated in FIGS. 2 and 3. The outer sector decreases in angle as the joint 30 is moved in extension from either of the positions in FIGS. 1 and 2 to the position shown in FIG. 3. The inner sector includes the are indicated by the arrows 70 and 72 in FIGS. 2 and 3. The inner sector decreases in angle as the joint 30 is moved in flexion from either of the positions shown in FIGS. 1 and 3 to the position shown in FIG. 2.

The bending mechanism 16 is connected with the back of the finger 18. Accordingly, the actuator mechanism 54 and the pivot connections 48 and 50 are disposed adjacent to the back of the finger 18. Thus, the bending mechanism 16, the actuator mechanism 54 and the pivot connections 48 and 50 are disposed in the outer sector indicated by the arrows 66 and 68.

Moving Finger in Flexion

When the input knob 56 is manually rotated in the direction of arrow 80 in FIG. 1, the actuator mechanism 54 is operated. Operation of the actuator mechanism 54 transmits force from the knob 56 to the actuator member 46. The actuator member 46 pivots the cuff arms 36 and 38 from the orientation shown in FIG. 1 toward the orientation shown in FIG. 2 to move the joint 30 in flexion.

Operation of the actuator mechanism 54 moves the inner end portions 42 and 44 of the cuff arms 36 and 38 away from the finger 18. This pivots the first cuff arm 38 in a counter-clockwise direction (as viewed in FIG. 2) about the pivot connection 48. Simultaneously therewith, the second cuff arm 38 pivots in a clockwise direction (as viewed in FIG. 2) about the pivot connection 50. As the cuff arms 36 and 38 are pivoted in opposite directions about the pivot connections 48 and 50 toward the orientation shown in FIG. 2, the joint 30 of the finger 18 is moved in flexion.

During pivotal movement of the cuff arms 36 and 38 and movement of the finger 18 in flexion, the actuator mechanism 54 transmits force to the finger cuffs 26 and 32. The cuffs 26 and 32 move along the cuff arms 36 and 38 away from the joint 30 and the pivot connections 48 and 50. Moving the finger cuffs 26 and 32 away from the joint 30 and the pivot connections 48 and 50 as the joint is moved in flexion greatly reduces the distractive forces applied to the soft tissue in the finger 18.

Figure 2:
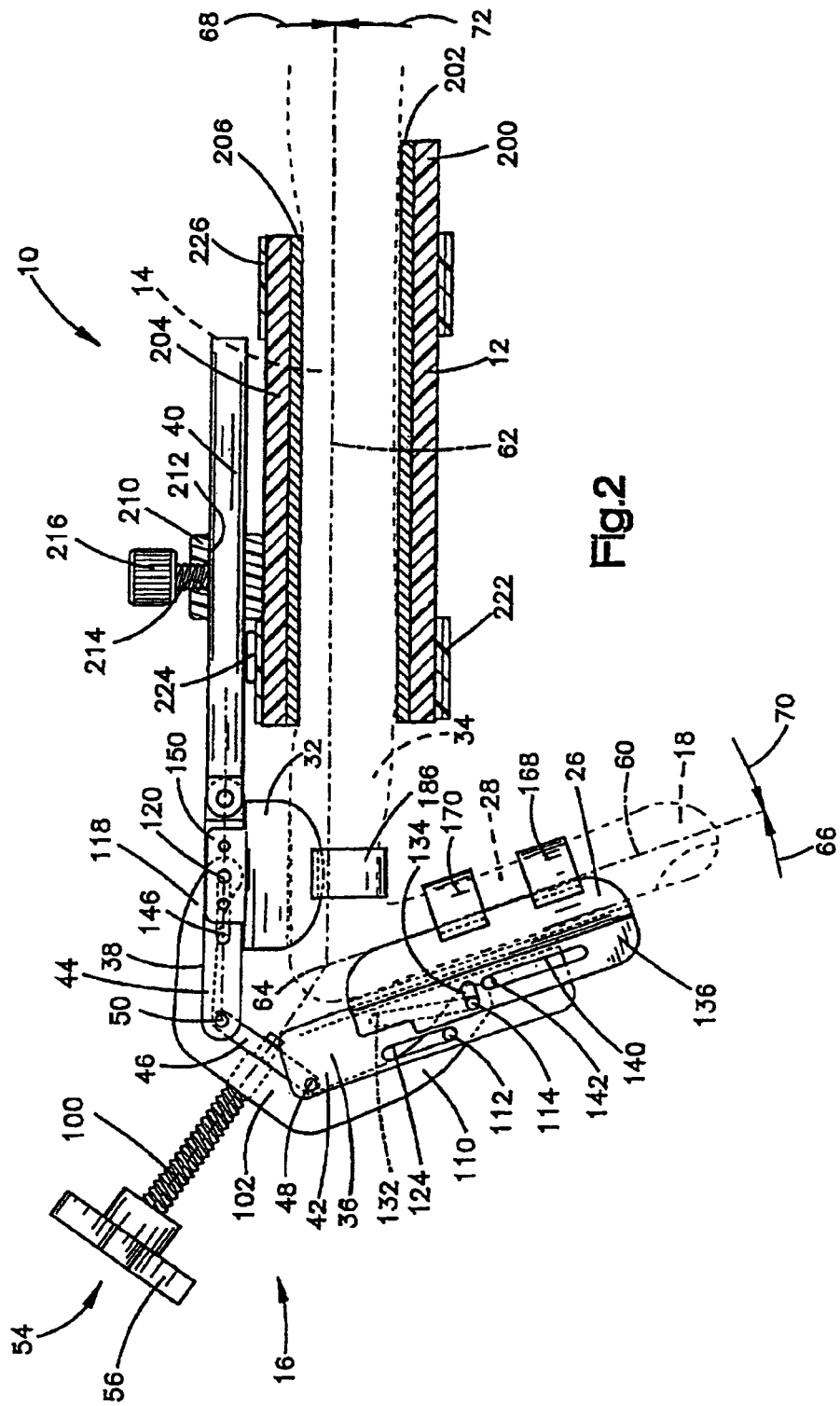
FIG. 2 is a schematic side view of the orthosis of FIG. 1 depicting the manner in which the orthosis of FIG. 1 is operated to bend the finger in flexion.

In the illustrated embodiment of the invention, the cuff arms 36 and 38 are moved by the actuator mechanism 54 through a range of movement from positions in which the cuff arms are positioned relative to each other as shown in FIG. 1 to a condition of maximum flexion in which the longitudinal axes of the cuff arms are disposed at an angle of approximately 70° C. relative to each other, as shown in FIG. 2. As the orthosis 10 is operated to move the finger 18 in flexion, the size of the inner sector, indicated by the arrows 70 and 72 is decreased and the size of the outer sector, indicated by the arrows 66 and 68 is increased. It should be understood that the foregoing specific range of movement of the orthosis 10 has been set forth herein for purposes of clarity of description and that it is contemplated that specific embodiments of the orthosis 10 will have finger cuffs 26 and 32 which move through different distances relative to each other and are movable to different angular orientations relative to each other.

It is contemplated that the specific procedure which is followed to move the finger 18 in flexion will vary depending upon the conditions of the finger and the desires of a surgeon or therapist supervising the use of the orthosis 10. However, it is believed that it may be preferred to use a static progressive stretch procedure during movement of the finger 18. This procedure is implemented by operating the actuator mechanism 54 to move the finger 18 in flexion to a limit of tolerance of the finger without severe pain. This position of the finger 18 is held for a period of time, for example, five minutes, to allow the tissue in the finger to relax. As the tissue relaxes, stress decreases. After the period of time has elapsed, the input member 56 is manually rotated to again stretch the soft tissue in the finger 18 to the limit of tolerance. This condition is again held for a period of time, for example, five minutes, to allow the tissue in the finger 18 to again relax. The process is repeated for the duration of a therapy session which, may be approximately 30 minutes long.

The input knob 56 may be manually rotated by either the patient, that is, the person having the hand 14 on which the orthosis 10 is mounted, or by a supervisory personnel, such as the therapist. However, it is believed that it will be desired to have the patient actuate the orthosis 10 to affect movement of the finger 18. The patient can feel when the tissue has tightened and the finger 18 has been moved to the limit of its tolerance, without severe pain. The patient can also feel when the tissue has relaxed and further actuation of the orthosis 10 to further move the finger 18 in flexion can be undertaken.

Although the foregoing description of moving a finger 18 in flexion with the orthosis 10 has been in conjunction with the movement of the index finger, it should be understood that the orthosis can be equally as well used to move any finger 18-24 of the hand 14 in flexion. Thus, the finger cuffs 26 and 32 are designed to enable them to be used to connect any of the fingers 18-24 of the hand 14 with the cuff arms 36 and 38. The hand cuff 14 is designed to enable the bending mechanism 16 to be connected with the hand cuff in alignment with any of the fingers 18-24. Furthermore, it is contemplated that bending mechanisms 16 can be connected with more than one of the fingers 18-24 at the same time to be used to sequentially move the fingers.

Moving Finger in Extension

When the finger 18 is to be moved in extension, the input knob 56 is manually rotated, in the direction of arrow 84 in FIG. 1, to operate the actuator mechanism 54. Operation of the actuator mechanism 54 transmits force from the input knob 56 to the actuator member 46. As the input knob 56 is manually rotated, the actuator mechanism 54 moves the actuator member 46 toward the finger 18. Thus, the end portions 42 and 44 of the cuff arms 36 and 38 are moved from the position shown in FIG. 1 toward the position shown in FIG. 3 as the input knob 56 is manually rotated.

As the end portions 42 and 44 of the cuff arms 36 and 38 are moved toward the finger 18, the cuff arms are pivoted in opposite directions about axes extending through the pivot connections 48 and 50. Thus, the cuff arm 38 is pivoted in a clockwise direction (as viewed in FIG. 3) about the pivot connection 48. The cuff arm 38 is pivoted in a counterclockwise direction about the pivot connection 50.

Figure 3:
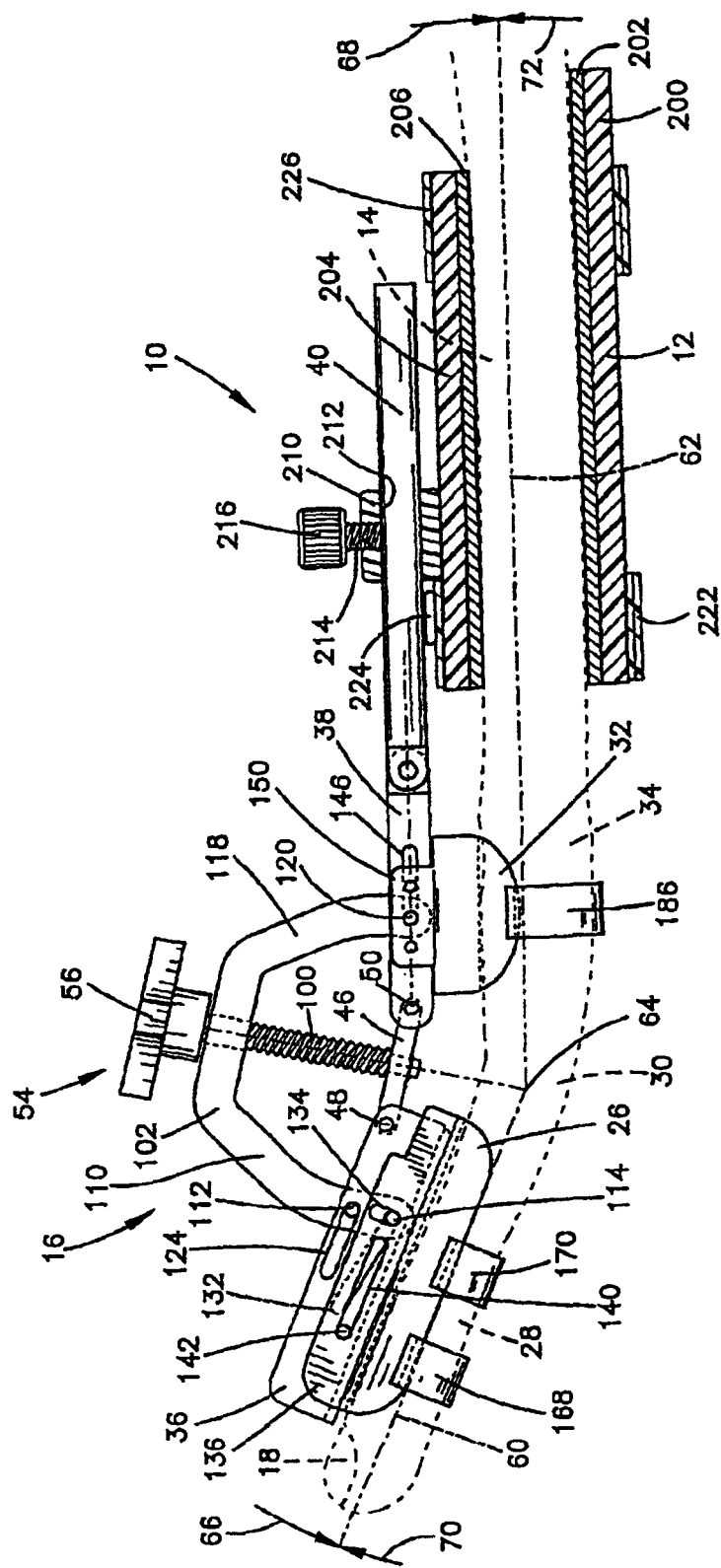
FIG. 3 is a schematic side view, generally similar to FIG. 2, of the orthosis depicting the manner in which the orthosis of FIG. 1 is operated to bend the finger in extension.

As the cuff arms 36 and 38 are pivoted about the pivot connections 48 and 50, the finger 18 is moved in extension from the initial condition shown in FIG. 1 toward the condition shown in FIG. 3. As this occurs, the outer sector, indicated by the arrows 66 and 68, decreases in size, and the inner sector, indicated by the arrows 70 and 72, increases in size. The cuff arms 36 and 38 are pivoted toward the actuator mechanism 54 in the outer sector.

As the cuff arms 36 and 38 (FIG. 3) are pivoted under the influence of force transmitted from the actuator mechanism 54 through the actuator member 46, the finger cuffs 26 and 32 are moved along the cuff arms 36 and 38. Thus, force is transmitted from the actuator mechanism 54 to the finger cuffs 26 and 32 to move the finger cuff along the cuff arms 36 and 38 toward the joint 30 and the pivot connections 48 and 50. The finger cuff 26 is moved along the cuff arm 38 toward the joint 30 and the pivot connection 48 as the cuff arm 38 is pivoted in a clockwise direction about the pivot connection 48. Similarly, the finger cuff 32 is moved along the cuff arm 38 toward the joint 30 and the pivot connection 50 as the cuff arm 38 is pivoted in a counterclockwise direction about the pivot connection 50. Moving the finger cuffs 26 and 32 toward the joint 30 and the pivot connections 48 and 50 minimizes the extent of distraction of the joint while ensuring that there is no compression of the finger 18.

It is believed that a static progressive stretch procedure may be preferred for moving the finger 18 in extension. Thus, the input knob or member 56 is manually rotated to operate the actuator mechanism 54 and effect pivoting of the cuff arms 36 and 38 to move the finger 18 in extension until the patient feels tissue tightness, but not severe pain. The orthosis 10 is maintained in that position for a period of time, which may be five minutes. When the tissue relaxes, the input member or knob 56 is again rotated to stretch the tissue. The steps of operating the orthosis 10 to stretch the tissue, interrupting operation of the orthosis to allow the tissue to relax and then again operating the orthosis to again stretch the tissue is repeated for the duration of a therapy session.

As was previously mentioned, the knob or input member 56 may be manually rotated by a therapist or surgeon. However, it is believed that it will be preferred to have the patient manually rotate the knob 56. Thus, the person having the hand 14 and finger 18 will rotate the knob 56 until he or she feels the tissue tighten and will further rotate the knob to further move the finger when he or she feels the tissue relax.

Although the foregoing description has been in conjunction with the moving of an index finger 18 in extension, it should be understood that the orthosis 10 may be used to move any of the fingers 18-24 of the hand 14 in extension. In the example of moving the finger 18 in extension illustrated in FIGS. 1 and 3, the finger is moved from an initial condition illustrated in FIG. 1. However, it is believed that, under certain circumstances, the finger 18 may initially be in the flex condition shown in FIG. 2 and moved in extension from the flex condition to the condition shown in FIG. 1. When this is to be done, the orthosis 10 is operated to move the finger 18 in extension toward the condition illustrated in FIG. 1.

Actuator Mechanism

The actuator mechanism 54 (FIGS. 2-5) is supported on the actuator member 46. The actuator mechanism 54 includes an externally threaded member or screw 100 which is rotatably supported within a frame 102. A central axis of the screw 100 extends through the center of the actuator member or base link 46 and through the center of the joint 30 with which the bending mechanism 16 is connected. A central axis of the screw 100 extends midway between and is perpendicular to parallel axes extending through the pivot connections 48 and 50.

The manually rotatable knob 56 is fixedly connected to the upper (as viewed in FIG. 1) end of screw 100. The frame 102 (FIGS. 2-5) has internal thread convolutions which engage with external thread convolutions on the screw 100. In the illustrated embodiment of the invention, the screw 100 is movable relative to the frame 102. However, the frame 102 could be movable relative to the screw 100. If this was done, the base link 46 would be connected with the frame 102.

Upon rotation of the input member or knob 56, the screw 100 is moved relative to the frame 102. As this occurs, the base link 46 pivots the cuff arms 36 and 38 about the pivot connections 48 and 50. Of course, pivotal movement of the cuff arms 36 and 38 moves the joint 30 of the finger 18 with which the orthosis 10 is connected. Movement of the screw 100 toward the joint 30 moves the joint in extension. Movement of the screw 100 away from the finger 18 moves the joint 30 in flexion.

The screw 100 and the base link 46 are moved from the initial condition shown in FIG. 1 to one of the actuated conditions shown in FIGS. 2 and 3. The screw 100 and base link 46 move along a linear path which extends perpendicular to the parallel axes through the pivot connections 48 and 50. The path along which the screw 100 and actuator member 46 move has a longitudinal central axis which is coincident to the central axis of the screw 100 and extends between the end portions 42 and 44 of the cuff arms 36 and 38.

In the illustrated embodiment of the invention, the screw 100 has a right-hand thread so that the knob 56 is manually rotated in a clockwise direction, as indicated by arrow 84 in FIG. 1, to move the screw 100 and base link 46 toward the finger 18. When the knob 56 is manually rotated in a counterclockwise direction, the screw 100 and the actuator member 46 move away from the finger 18. It should be understood that an input member other than the knob 56 could be used to operate the actuator mechanism 54 if desired.

The frame 102 (FIGS. 2-5) has a first end 110 pivotally connected with the cuff arm 38 at a pivot connection 112. The end 110 of the frame 102 is also pivotally connected to the finger cuff 26 and the cuff arm 38 at a pivot connection 114. The end 110 of the frame 102 extends between side walls 116 (FIGS. 4 and 5) of the cuff arm 38. The frame 102 has a second end 118 pivotally connected with the cuff arm 38 and the finger cuff 32 at a pivot connection 120. The end 118 of the frame 102 extends between side walls 122 of the cuff arm 38.

The cuff arm 36 has slots 124 (FIGS. 4 and 5) in the side walls 116. A pin 126 extends through the slots 124 and the end 110 of the frame 102. The pin 126 connects the end 110 of the frame 102 with the cuff arm 38 at the pivot connection 112. The pin 126 is movable relative to the cuff arm 36 along the slot 124.

The cuff arm 36 also has slots 132 in the side walls 116 which extend at angles to the slots 124. The finger cuff 26 has slots 134 in side walls 136 that extend perpendicular to the slots 124 and at an angle to the slots 132. A pin 138 extends through the slots 132 and 134 and the end 110 of the frame 102. The pin 138 connects the end 110 of the frame 102 with the cuff arm 38 and the cuff 26 at the pivot connection 114. The pin 138 is movable relative to the slots 132 in the cuff arm 38 and the slots 134 in the finger cuff 26.

The finger cuff 26 has slots 140 in the side walls 136 extending perpendicular to the slots 134 and parallel to the slots 124. A pin 142 extends through the cuff arm 38 and the slots 140 to guide movement of the cuff 26 relative to the cuff arm 36. The pin 142 is movable along the slots 140 relative to the finger cuff 26.

The cuff arm 36 (FIGS. 4 and 5) extends between the side walls 136 of the cuff 26. The side walls 136 of the cuff 26 engage the side, walls 116 of the cuff arm 36. The side walls 116 of the cuff arm 36 guide movement of the cuff 26 relative to the cuff arm 36.

The cuff arm 38 (FIGS. 4 and 5) has slots 146 in the side walls 122. A pin 148 extends through the slots 146, the cuff 32 and the end 118 of the frame 102. The pin 148 connects the finger cuff 32 with the cuff arm 38 and the frame 102 at the pivot connection 120. The pin 148 extends through side walls 150 of the cuff 32. The pin 148 is movable along the slots 146 to guide movement of the cuff 32 relative to the cuff arm 38.

The side walls 150 of the cuff 32 have openings 152 and 154 on opposite sides of the pin 148. The pin 148 could extend through the openings 152 or 154 instead of extending through the cuff 32 at the location between the openings. Accordingly, the pin 148 can connect the finger cuff 32 to the cuff arm 38 and the end 118 of the frame 102 at any of three locations.

The cuff arm 38 extends between the side walls 150 of the cuff 32. The side walls 150 of the cuff 32 engage the side walls 122 of the cuff arm 38. The side walls 122 of the cuff arm 38 guide movement of the cuff 32 relative to the cuff arm 38.

Upon manual rotation of the input member or knob 56 in a clockwise direction, the screw 100 is rotated to move the base link 46 toward the finger 18 (FIG. 3). As this occurs, the cuff arm 38 is pivoted in a clockwise direction about the pivot connection 48 and transmits force to the pivot connections 112 and 114. The force transmitted from the base link 46 to the pivot connections 112 and 114 pivots the cuff arm 38 and cuff 26 in a clockwise direction about axes extending through the pivot connections 112 and 114. This results in the cuff arm 38 pivoting from the initial position shown in FIG. 1 to the actuated position shown in FIG. 3 as the screw 100 moves relative to the frame 102.

As the cuff arm 38 (FIG. 5) pivots about the pivot connections 112 and 114, the pin 126 moves along the slots 124 toward the right, as viewed in FIG. 5. The pin 138 moves toward the right as viewed in FIG. 5, along the slots 132. The pin 138 also moves downward, as viewed in FIG. 5, along the slots 134. This results in the finger cuff 26 moving relative to the cuff arm 38 toward the joint 30.

As the screw 100 and base link 46 move toward the finger 18, the cuff arm 38 is pivoted in a counterclockwise direction relative to the base link 46 and force is transmitted to the pivot connection 120. The force transmitted to the pivot connection 120 pivots the cuff arm 38 relative to the second end 118 of the frame 102. As the cuff arm 38 pivots about the pivot connection 120 relative to the second end 118 of the frame 102, the pin 148 moves toward the left, as viewed in FIG. 5, along the slots 146 and the finger cuff 32 moves relative to the cuff arm 38.

Figure 4:
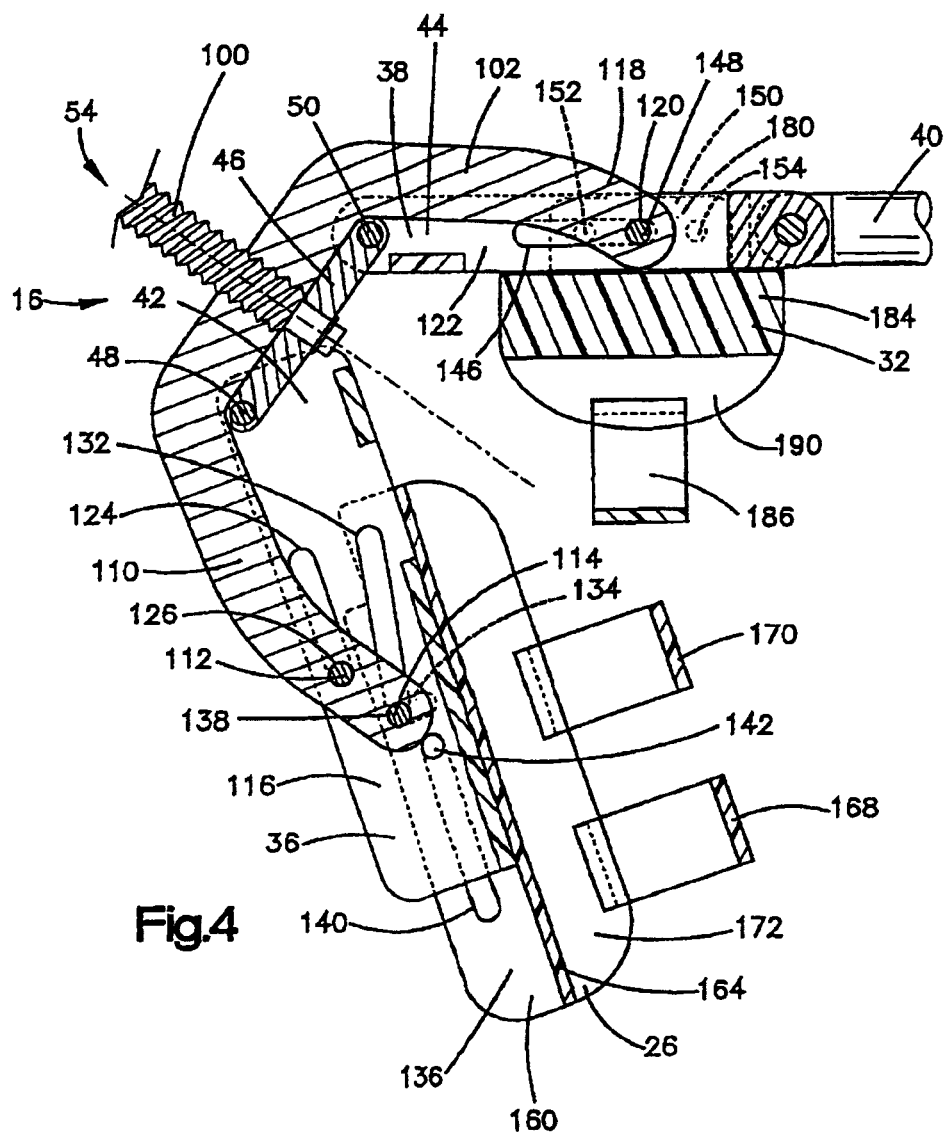
FIG. 4 is an enlarged sectional view of a portion of the orthosis of FIG. 1 depicting the manner in which the orthosis is operated to move the finger in flexion.

Upon manual rotation of the input member or knob 56 in a counterclockwise direction, the screw 100 is rotated to move away from the finger 18 (FIGS. 2 and 4). As this occurs, the cuff arm 36 is pivoted in a counterclockwise direction about the pivot connection 48 and force is transmitted to the pivot connections 112 and 114 between the cuff arm 36 and the first end 110 of the frame 102. The force transmitted to the pivot connections 112 and 114 pivots the cuff arm 36 in a counterclockwise direction about the pivot connections 112 and 114. This results in the pin 126 moving downward, as viewed in FIG. 4, along the slots 124. The pin 138 moves downward as viewed in FIG. 4, along the slots 132. The pin 138 also moves toward the left, as viewed in FIG. 4, along the slots 134. The pin 142 moves upward along the slots 140 as the finger cuff 26 moves away from the joint 30.

As the input member or knob 56 is rotated in the counterclockwise direction, the cuff arm 38 is pivoted in a clockwise direction about the pivot connection so and force is transmitted to the pivot connection 120 between the first end 118 of the frame 102 and the cuff arm 38. The force transmitted to the pivot connection 120 pivots the cuff arm 38 in a clockwise direction about the pivot connection 120. This results in the pin 148 moving toward the right, as viewed in FIG. 4, along the slots 146 and the finger cuff 32 moving away from the joint 30.

Cuff Adaptors

The finger cuff 26 (FIGS. 4 and 5) includes a channel-shaped portion 160 for receiving the cuff arm 36. The channel-shaped portion 160 is defined by the parallel side walls 136 extending perpendicular to a base 164. The base 164 can be placed in engagement with a back of the portion 28 of the finger 18. Suitable straps 168 and 170 extend through retainers 172 extending from the base 164 to secure the finger cuff 26 with the finger 18, as seen in FIG. 1.

The finger cuff 32 (FIGS. 4 and 5) has a channel-shaped portion 180 which receives the cuff arm 38. The channel-shaped portion 180 is defined by the side walls 150 extending perpendicular to a base 184. The base 184 is placed in engagement with a back of the portion 34 of the finger 18. A suitable strap 186 extends through a retainer portion 190 extending from the base 184 to secure the finger cuff 32 with the finger 18, as seen in FIG. 1.

The hand cuff 12 has a first plate 200 (FIGS. 1-3) with padding 202 which is mounted on a palm of the hand 14. A second plate 204 with padding 206 is mounted on the back of the hand 14 opposite from the palm. Four cylindrical members 210 are fixedly connected with the second plate 204. Each of the cylindrical members 210 is aligned with one of the fingers 18-24 of the hand 14. The cylindrical members 210 have axially extending openings 212 for receiving the connecting portion 40 of the bending mechanism 16. Threaded openings 214 in the cylindrical members 210 extend transverse to the axis of the cylindrical members. A set screw 216 threadably engages the opening 214 in the cylindrical member 210 to clamp the connecting portion 40 to the cylindrical member.

A suitable strap 222 is fixedly connected to the plate 204 by rivets 224. Another strap 226 extends around the plates 200 and 204 adjacent the heel of the hand 14. The straps 222 and 226 secure the plates 200 and 204 to the hand 14 using hook and loop connectors.

Conclusion

The present invention provides a new and improved method for using an orthosis 10 to sequentially move different fingers of a hand. When the orthosis 10 is to be used to move a finger of the hand, a bending mechanism 16 is connected with a back of the finger. The bending mechanism 16 is operated to move a joint of the finger. An actuator member 46 of the bending mechanism 16 is moved along a path extending through the joint to move the joint. The bending mechanism 16 can be connected with another finger of the hand to move the other finger or a second bending mechanism can be connected with the other finger to move the other finger.

From the above description of the invention, those skilled in the art will perceive improvements, changes and modifications. Such improvements, changes and modifications within the skill of the art are intended to be covered by the appended claims.

What is claimed is:

1. A finger orthosis for moving a joint of a finger, the finger orthosis comprising:
a hand cuff configured to couple to a hand connected to a finger; and
an actuating mechanism coupled to the hand cuff, the actuating mechanism comprising an actuator member, an externally threaded member, and a frame, a pair of finger cuffs attached to said actuator member, said actuator member being slidable along a longitudinal axis of said handcuff.

2. The finger orthosis of claim 1, wherein a rotatable knob is connected to the externally threaded member.

3. The finger orthosis of claim 1, wherein the frame comprises internal thread convolutions that engage with the externally threaded member.

4. The finger orthosis of claim 1, wherein the externally threaded member is movable relative to the frame.

5. The finger orthosis of claim 1, wherein the frame is movable relative to the externally threaded member.

6. The finger orthosis of claim 1, wherein the frame has a first end connected with said pair of finger cuffs and a second end connected with said pair of finger cuffs.

7. A method of using a finger orthosis to move a joint between first and second portions of a finger, the method comprising:
coupling a hand cuff to a hand, wherein the hand is connected to a finger, and
applying force to an actuating mechanism coupled to the hand cuff, the actuating mechanism comprising an actuator member, an externally threaded member, a frame and a pair of finger cuffs attached to said actuator member,
wherein applying the force to the actuating mechanism causes the actuator member to slide along a longitudinal axis of said handcuff.

8. The method of claim 7, wherein moving the actuator member causes the finger to move in extension.

9. The method of claim 7, wherein moving the actuator member causes the finger to move in flexion.

10. The method of claim 7, wherein the frame comprises internal thread convolutions that engage with the externally threaded member.

11. The method of claim 7, wherein the externally threaded member is movable relative to the frame.

12. The method of claim 7, wherein the frame is movable relative to the externally threaded member.

* * * * *